(12) United States Patent
Liu et al.

(10) Patent No.: US 6,218,574 B1
(45) Date of Patent: Apr. 17, 2001

(54) PROCESS FOR PURIFYING LONG-CHAIN DICARBOXYLIC ACID

(75) Inventors: Shuchen Liu; Dacheng Gao; Jiangang Zhang, all of Fushun (CN)

(73) Assignees: China Petrochemical Corporation, Beijing; Fushun Research Institute of Petroleum & Petrochemical, Fushun, both of (CN)

( * ) Notice: Subject to any disclaimer, the term of this patent is extended or adjusted under 35 U.S.C. 154(b) by 0 days.

(21) Appl. No.: 09/453,081

(22) Filed: Dec. 2, 1999

(30) Foreign Application Priority Data

Dec. 3, 1998 (CN) .......................................... 98 1 21048.1

(51) Int. Cl.[7] .................................................... C07C 51/42
(52) U.S. Cl. ............................................................ 562/593
(58) Field of Search ............................................... 562/593

(56) References Cited

FOREIGN PATENT DOCUMENTS

| 56-26193 | 3/1981 | (JP) . |
|---|---|---|
| 56-26194 | 3/1981 | (JP) . |

*Primary Examiner*—Gary Geist
*Assistant Examiner*—John N. Calve
(74) *Attorney, Agent, or Firm*—Shanks & Herbert

(57) ABSTRACT

The present invention relates to an aqueous phase process for purifying long-chain dicarboxylic acids from a liquid containing a long-chain dicarboxylic acid/or a salt thereof. The invention overcomes the disadvantages of low purity and high chroma of the product obtained by using the aqueous phase process of the prior art. Through the step of crystallizing the monosalt of long-chain dicarboxylic acid, the present process reduces effectively the content of such impurities as proteins and coloring materials in the product and obtains the long-chain dicarboxylic acid product having a total acid content of greater than 99 wt % and exhibiting a white appearance.

10 Claims, No Drawings

PROCESS FOR PURIFYING LONG-CHAIN DICARBOXYLIC ACID

The present invention relates to a process for purifying long-chain dicarboxylic acid, more particularly, a process for purifying long-chain dicarboxylic acid from a liquid containing a long-chain dicarboxylic acid and/or a salt thereof.

Long-chain dicarboxylic acid is a metabolic product obtainable from the fermentation of n-alkane by microorganisms. The fermentation liquid is a complex multi-phase system which contains unreacted n-alkane, cells of microorganisms and fragments thereof, unutilized culture medium and metabolites, secretion substances of the microorganism and the like, especially in which a large amount of impurities, such as proteins and coloring materials, will have serious adverse effect on the purity and appearance of the product.

At present, the process for purifying the long-chain dicarboxylic acid is typically classified into two types: a solvent process and an aqueous phase process. Though the problems mentioned above can be solved by using the solvent process, its application is significantly restricted by the problems such as high investment, residual alkane and solvent in the product, safety of production and so on. The aqueous phase process can overcome the defects that the solvent process has, but the purity and color appearance of its product cannot attain to a higher level. For example, JP56026193 and JP56026194 disclose an aqueous phase process for separating dicarboxylic acid, wherein the operation steps comprise alkalifying and stewing the end fermentation liquid, centrifuging to remove mycelia, adding siliceous earth to adsorb unreacted reactants and by-products, then filtering, acidifying and crystallizing the filtrate. Finally, the product of dicarboxylic acid is obtained after filtration and drying. The main problem existing in the processes mentioned above is the autolysis of cells during alkalifying and stewing, thereby the impurities such as proteins and coloring materials in cells are dissolved into the fermentation liquid, consequently the purity of total dicarboxylic acid product is only 98.5% at highest, and the coloring materials in the product are difficult to be removed. The product is then light tawny in appearance.

The object of the present invention is to provide an aqueous phase process for purifying long-chain dicarboxylic acid from a liquid containing a long-chain dicarboxylic acid and/or a salt thereof so as to improve the purity of product, decrease the chroma of product and provide the product with higher quality.

Directing to the defects existing in the prior art, the present invention further purifies long-chain dicarboxylic acid product by using crystallization of monosalt of long-chain dicarboxylic acid. It has been found upon research that the monosalt of long-chain dicarboxylic acid has very weak ability to adsorb the coloring materials. Consequently, during crystallization of monosalt of the long-chain dicarboxylic acid, the soluble proteins and coloring materials remain in the mother liquid when the monosalt of long-chain dicarboxylic acid is filtered. So this process has a dual function of removing both proteins and coloring materials, thus the purity of the long-chain dicarboxylic acid product is improved and the chroma of the product decreases.

Thus the present invention provides a process for purifying long-chain dicarboxylic acid from a liquid containing a long-chain dicarboxylic acid and/or a salt thereof comprising the steps of:

I. adjusting the pH value of said liquid containing a long-chain dicarboxylic acid and/or a salt thereof to 6.2–7.0 to form a monosalt of long-chain dicarboxylic acid;

II. dissolving the monosalt of long-chain dicarboxylic acid by heating to obtain a solution containing the monosalt of long-chain dicarboxylic acid;

III. crystallizing the solution obtained from the above step by cooling, and filtering the solution to obtain a filter cake of the monosalt of long-chain dicarboxylic acid and a filtrate;

IV. dissolving the filter cake of the monosalt of long-chain dicarboxylic acid obtained in the above step by heating;

V. converting the monosalt of long-chain acid into long-chain dicarboxylic acid; and VI isolating the long-chain dicarboxylic acid.

The present invention is suitable for use with any liquid that contains a long-chain dicarboxylic acid and/or a salt thereof. An example of such a liquid is the fermentation liquid obtained through fermentation of an n-alkane by microorganisms.

The present invention applies to any long-chain dicarboxylic acid. Preferably, the long-chain dicarboxylic acid may be a $C_{10}$–$C_{18}$ long-chain dicarboxylic acid or a mixture of $C_{10}$–$C_{18}$ long-chain dicarboxylic acids.

The present invention utilizes a distinct property of the monosalt of long-chain dicarboxylic acid, that is, its weak ability to adsorb the coloring materials. So it is important to properly adjust the pH value of the liquid so as to ensure that the dicarboxylic acid is converted into its monosalt form completely. Suitable pH value is from 6.2 to 7.0, preferably from 6.5 to 6.8. Acids and bases used to adjust the pH value are those which are commonly used in the art for this purpose, including organic and inorganic acids and bases. Examples of such acids are sulfuric acid, nitric acid, hydrochloric acid and phosphoric acid. Examples of such bases are alkali metal hydroxides, such as sodium hydroxide and potassium hydroxide.

Where the liquid from which the long-chain dicarboxylic acid to be purified is a fermentation liquid of an n-alkane, said liquid is advantageously treated by conventional method to remove the mycelia which may be present in the liquid prior to being processed by the process of the present invention. The treated liquid may be adjusted with an acid to 6.2–7.0. Alternatively, said fermentation liquid may be acidified directly, for example to a pH value of 2.0–4.0, preferably with heating, without removal of the mycelia. This may cause some of the proteins in the fermentation liquid to be denatured and precipitated. Then, the acidified liquid may be filtered to obtain a filter cake of long-chain dicarboxylic acid containing mycelia, leaving soluble proteins and part of the coloring materials in the filtrate. Optionally, alkanes remaining in the fermentation liquid may be separated from the liquid before the filtration is carried out. An alkali solution is added to the filter cake to obtain a liquid that is now ready to be processed by the process of the present invention.

After the dicarboxylic acid is converted into its monosalt form by pH adjustment, said liquid is heated by conventional means to dissolve the monosalt of the dicarboxylic acid. The solution obtained is cooled such that the monosalt of dicarboxylic acid is crystallized from the solution. Alternatively, the solution containing the monosalt of long-chain dicarboxylic acid is filtered to remove solids prior to being crystallized.

After crystallization, the solution is filtered to obtain a filter cake of the monosalt of dicarboxylic acid and a filtrate. The filter cake obtained is dissolved in an aqueous solvent (for example, water), preferably with heating. The filtrate obtained may be treated with an adsorbent to remove coloring materials and soluble proteins. The treated filtrate may be used for dissolving the filter cake mentioned above. Said adsorbent is selected from conventional adsorbents which are suitable for the removal of coloring materials and soluble proteins, for example, active carbon and active clay. The amount of the adsorbent added may be 0.5–3% by weight based on the weight of the filtrate and the treatment with the adsorbent may be carried out at 20–60° C. for 15–30 minutes.

After the filter cake of the monosalt of dicarboxylic acid is completely dissolved, the monosalt of dicarboxylic acid is converted to its acid form by any of conventional methods. For example, the monosalt may be acidified with an acid to a pH value of 2.0–4.0, preferably with heating to 80–95° C.

Alternatively, where a fermentation liquid is acidified directly prior to being processed by the process of the present invention, the monosalt of the dicarboxylic acid may be converted to its acid form by the following steps:

a). adding an alkali to form completely a solution of disalt of long-chain dicarboxylic acid;
  b). filtering off the solids; and
  c). acidifying the filtrate obtained in the above step to convert the disalt of long-chain dicarboxylic acid into long-chain dicarboxylic acid completely.

The last step of the present invention is to isolate the long-chain dicarboxylic acid. In this connection, conventional methods that are well known in the art may be used, for example, crystallization, filtration, washing, drying and so on.

In an embodiment of the invention, the following procedures may be followed:

1. Adding an acid to the filtrate, which is obtained after an end fermentation liquid of an n-alkane is filtered and mycelia are removed, to adjust its pH value to 6.2–7.0, then heating it to 85–100° C. to dissolve completely the formed monosalt of long-chain dicarboxylic acid, and subsequently reducing the temperature to 75–85° C. and maintaining the temperature for 15–30 minutes.
  2. Cooling the resultant solution to room temperature, and filtering to obtain a filter cake of the monosalt of long-chain dicarboxylic acid and a filtrate.
  3. dissolving the monosalt of long-chain dicarboxylic acid and adding an acid to the resultant solution to adjust its pH value to 2.0–4.0, and heating the solution to 80–95° C. to convert the monosalt of long-chain dicarboxylic acid into the long-chain dicarboxylic acid completely, then reducing the temperature to 70–85° C., and maintaining the temperature for 15–30 minutes.
  4. Cooling and crystallizing the solution obtained in step 3, and obtaining a purified product of the long-chain dicarboxylic acid through the steps of filtering, washing and drying and so on.

Wherein the pH value of the solution acidified in step 1 is controlled preferably in the range of 6.5–6.8. 0.5–3 Wt % of an adsorbent can be added to the filtrate obtained in step 2 to remove coloring materials and soluble proteins. The adsorption treatment is carried out at 20–60° C. for 15–30 minutes. Then the mixture is filtered to obtain the filtrate decolorized and deproteinized. The resultant filtrate is used for dissolving the filter cake in step 3.

In another embodiment of the invention, the following procedures may be followed:

1. Acidifying directly an end fermentation liquid of an n-alkane, adjusting the pH value of the resultant solution to 2–4, then heating it to 75–90° C., separating and recovering alkane at a standstill, then reducing slowly the temperature to room temperature, and filtering to obtain a filter cake of long-chain dicarboxylic acid containing mycelia.
  2. Mixing the filter cake of long-chain dicarboxylic acid containing mycelia with water, adding an alkali to the resultant mixture to adjust its pH value to 6.2–7.0, then heating to 85–100° C. to dissolve completely the formed monosalt of long-chain dicarboxylic acid, and reducing the temperature of the resultant solution to 75–85° C. and maintaining the temperature for 15–30 minutes.
  3. Reducing slowly the temperature of the solution obtained in step 2 to room temperature in order to promote the crystallization of the monosalt of long-chain dicarboxylic acid, and filtering to obtain a filter cake of the monosalt of long-chain dicarboxylic acid containing mycelia and a filtrate.
  4. Dissolving the filter cake obtained in step 3, adding an alkali solution to adjust its pH value to 9–12, then heating it slowly to 50–70° C. to form completely a solution of the disalt of long-chain dicarboxylic acid, and filtering to obtain a clarified filtrate of the disalt of long-chain dicarboxylic acid.
  5. Acidifying the clarified filtrate of the disalt of long-chain dicarboxylic acid obtained in step 4 by adding an acid, adjusting its pH value to 2–4, and heating it to 75–95° C. to convert the disalt of long-chain dicarboxylic acid into long-chain dicarboxylic acid completely, thereafter decreasing the temperature to 70–85° C. and maintaining the temperature for 15–30 minutes, and then cooling slowly to room temperature, and obtaining a purified long-chain dicarboxylic acid product through the steps of filtering, washing and drying.

Wherein the filtrate obtained in step 3 may be treated with 0.5–3 wt % of an adsorbent at 20–60° C. for 15–30 minutes, and filtered to obtain a clarified filtrate which is then used for dissolving the filter cake in step 4. In step 4, in order to reduce the filtration time, 1–3 wt % of a filter aid may be added to the solution and mixed thoroughly prior to filtration.

In still another embodiment of the invention, the following procedures may be followed:

1. Acidifying directly an end fermentation liquid of an n-alkane to adjust its pH value to 2–4, heating to 75–90° C., separating and recovering alkane at a standstill, then reducing slowly the temperature to room temperature, and filtering slowly the temperature to room temperature, and filtering to obtain a filter cake of long-chain dicarboxylic acid containing mycelia.
  2. Mixing the filter cake of the long-chain dicarboxylic acid containing mycelia with water, wadding an alkali to adjust its pH value to 6.2–7.0, then heating to 85–100° C. to dissolve completely the formed monosalt of long-chain dicarboxylic acid.
  3. Filtering the solution obtained in step 2 to obtain a filtrate containing the monosalt of long-chain dicarboxylic acid.
  4. Maintaining the temperature of the filtrate obtained in step 3 at 75–85° C. for 15–3 minutes, then reducing the temperature slowly to room temperature to crystallize the monosalt of long-chain dicarboxylic acid, and filtering to obtain a filter cake of the monosalt of long-chain dicarboxylic acid and a filtrate.
  5. Dissolving the filter cake obtained in step 4 and adding an acid to adjust the pH value to 2.0–4.0, and heating to 80–95° C. to convert the monosalt of long-chain dicarboxylic acid into the long-chain dicarboxylic acid completely, then reducing the temperature to 70–85° C. and maintaining this temperature for 15–30 minutes, then cooling and crystallizing, and obtaining a purified product of long-chain dicarboxylic acid through the steps of filtering, washing, drying and so on.

Wherein the filtrate obtained in step 4 may be treated with 0.5–3 wt % of an adsorbent at 20–60° C. for 15–30 minutes, and filtered to obtain a clarified filtrate which is then used for dissolving the filter cake in step 5. In step 3, in order to reduce the filtration time, 1–3 wt % of a filter aid may be added to the solution and mixed thoroughly prior to filtration.

The acid used for acidification as mentioned above according to the invention may be $H_2SO_4$, $HNO_3$, HCl or $H_3PO_4$, and the alkali used may be an alkali metal hydroxide, such as NaOH, KOH and the like. The adsorbent used may be active carbon or active clay, and the filter aid used may be siliceous earth.

In the process according to the present invention, when the monosalt of long-chain dicarboxylic acid is to be crystallized and when the final acidification and crystallization is to be carried out to obtain the purified dicarboxylic acid, it is preferable that the temperature be controlled and maintained at 75–85° C. for 15–30 minutes, and then reduced slowly to promote the crystal growth. This facilitates not only the operation of filtration, but also retention of coloring materials and soluble proteins in the filtrate. In addition, since the monosalt of long-chain dicarboxylic acid has very weak ability to adsorb coloring materials and proteins, the proteins and coloring materials remain in the filtrate when the monosalt of the long-chain dicarboxylic acid is crystallized and filtered, so that the proteins and coloring materials can be removed by adding an adsorbent into the filtrate. The long-chain dicarboxylic acid prepared according to the process of the present invention has a total acid purity of higher than 99 wt %, a nitrogen content of less than 50 μg/g, a yield of greater than 90 wt %, a chroma of less than 40, and the product exhibits a white appearance. The long-chain dicarboxylic acid prepared according to the process of the present invention can be widely used for synthesizing such products as high-grade perfume and advanced thermosol and so on.

The present invention will be illustrated by the following examples.

EXAMPLE 1

200 Ml of a fermentation liquid having a concentration of 124 g/l of $C_{10}$ dicarboxylic acid and a pH value of 7.9, which had been fermented with *candida tropicalis*, was treated for removal of mycelia. 3 Mol/l of $H_2SO_4$ was added thereto to adjust its pH value to 6.5. The mixture was then heated to 93° C., thereafter the temperature was reduced to and maintained at 80° C. for 30 minutes, and then reduced slowly to room temperature. After filtration, a filter cake of the monosodium salt of dicarboxylic acid and a filtrate were obtained.

1 Wt % of active carbon powder was added to the filtrate and the filtrate was treated for adsorption at 40° C. for 30 minutes, then filtered again to obtain another filtrate, which was then mixed with the above filter cake by adding 150 ml of water. To the resultant mixture was added 3 mol/l of $H_2SO_4$ to adjust the pH value to 3.0, then heated to 80° C. and stirred throroughly, and subsequently cooled at a standstill to room temperature, filtered, washed and dried to obtain a purified $C_{10}$ dicarboxylic acid product. The properties of the product are shown in Table 1.

EXAMPLE 2

To 200 ml of a fermentation liquid having a concentration of 130 g/l of $C_{13}$ dicarboxylic acid and a pH value of 7.6, which had been fermented with *candida tropicalis*, was added 3 mol/l of $H_2SO_4$ to adjust its pH value to 4.0, heated to 80° C. and placed at a standstill for 30 minutes. Then the alkane remaining in the solution was removed, and the temperature of the solution was reduced to room temperature. After filtration and washing, a crude filter cake of $C_{13}$ dicarboxylic acid containing mycelia was obtained.

The crude filter cake was blended with 325 ml of water. To the resultant mixture was added 10 mol/l of NaOH solution to adjust its pH value to 6.5, and heated to 95° C., then cooled to and maintained at 80° C. for 30 minutes, and then cooled slowly to room temperature. After filtration, a filter cake of the monosodium salt of $C_{13}$ dicarboxylic acid and a filtrate were obtained. 1 Wt % of active carbon powder was added to the filtrate and the filtrate was treated for adsorption at 40° C. for 30 minutes. The filtrate obtained by the filtration was mixed with the filter cake of the monosodium salt of $C_{13}$ dicarboxylic acid. 10 Mol/l of NaOH was added to adjust the pH value to 10.2. The resultant mixture was heated to 60° C. to form the disodium salt of $C_{13}$ dicarboxylic acid. Then 2 wt % of siliceous earth was added as a filter aid and mixed thoroughly. After filtering off solids, a filtrate was obtained. Subsequently 3 mol/l of $H_2SO_4$ was added to the filtrate to adjust its pH value to 4.0. after heating to 80° C. and cooling at a standstill to room temperature, $C_{13}$ dicarboxylic acid was obtained which was then filtered, washed and dried to obtain a purified $C_{13}$ dicarboxylic acid product. The properties of the product are shown in Table 1.

EXAMPLE 3

200 Ml of a fermentation liquid having a concentration of 130 g/l of $C_{13}$ dicarboxylic acid and a pH value of 7.6 was treated for removal of mycelia. 3 Mol/l of $H_2SO_4$ was added thereto to adjust its pH value to 6.2, then heated to 95° C., thereafter the temperature was reduced to and maintained at 80° C. for 30 minutes, and then reduced slowly to room temperature. After filtration, a filter cake of the monosalt of $C_{13}$ dicarboxylic acid and a filtrate were obtained.

1 Wt % of active carbon powder was added to the filtrate and the filtrate was treated for adsorption at 40° C. for 30 minutes, then filtered again to obtain another filtrate, which was then mixed with the above filter cake by adding 150 ml of water. To the resultant mixture was added 3 mol/l of $H_2SO_4$ to adjust its pH value to 3.2, then heated to 80° C. and mixed thoroughly, and subsequently cooled at a standstill to room temperature. After filtration, washing and drying, a purified $C_{13}$ dicarboxylic acid product was obtained. The properties of the product are shown in Table 1.

EXAMPLE 4

To 200 ml of a fermentation liquid having a concentration of 120 g/l of the mixed dicarboxylic acids of $C_{13}$ and $C_{14}$ and a pH value of 7.6, which had been fermented with *candida tropicalis*, was added 3 mol/l of $H_2SO_4$ to adjust its pH value to 3.4, then heated to 80° C. at a standstill for 30 minutes. The $C_{13}$ and $C_{14}$ alkanes remaining in the solution were removed, then the resultant solution was cooled to room temperature. After filtration and washing, a filter cake of mixed dicarboxylic acids containing mycelia was obtained.

200 Ml of water was added to the filter cake and mixed thoroughly. To the resultant mixture was added 10 mol/l of NaOH to adjust its pH value to 6.6, and heated to 95° C., then cooled to and maintained at 80° C. for 30 minutes, subsequently, cooled slowly to room temperature. After filtration, a filter cake of the monosodium salt of mixed long-chain dicarboxylic acids and a filtrate were obtained. 1 Wt % of active carbon powder was added to the filtrate and the filtrate was treated for adsorption at 40° C. for 30 minutes. The filtrate was filtered again to obtain another filtrate that was then mixed with the above filter cake. To the resultant mixture was added 10 mol/l of NaOH to adjust its pH value to 9.7, and heated to 60° C., then 2 wt % of siliceous earth was added and stirred thoroughly. The solids were filtered off. 3 Mol/l of $H_2SO_4$ was added to the filtrate to adjust its pH value to 3.0, then heated to 80° C., and subsequently cooled at a standstill to room temperature. After filtration, washing and drying, a purified mixed long-chain dicarboxylic acid product was obtained. The properties of the product are shown in Table 1.

EXAMPLE 5

To 400 ml of a fermentation liquid having a concentration of 130 g/l $C_{13}$ dicarboxylic acid and a pH value of 7.5, which had been fermented with *candida tropicalis,* was added 3 mol/l of $H_2SO_4$ to adjust its pH value to 4.0, then heated to 80° C. and placed at a standstill for 30 minutes. Then the alkane remaining in the solution was separated, and the temperature of the solution was reduced to room temperature. After filtration and washing, a crude filter cake of $C_{13}$ dicarboxylic acid containing mycelia was obtained.

The crude filter cake of $C_3$ dicarboxylic acid was mixed with 650 ml of water. To the resultant mixture was added 10 mol/l of NaOH to adjust its pH value to 6.6, and heated to 96° C. to dissolve completely the monosodium salt of $C_{13}$ dicarboxylic acid. Then the solids were filtered off. The filtrate was cooled to 80° C. and maintained at the temperature for 20 minutes, then cooled slowly to room temperature, and filtered to obtain a filter cake of monosodium salt of $C_{13}$ dicarboxylic acid and a filtrate. 1.8 Wt % of active carbon powder was added to the filtrate and the filtrate was treated for adsorption at 50° C. for 20 minutes. The filtrate was filtered again to obtain another filtrate that was then mixed with the filter cake of the monosodium salt of $C_{13}$ dicarboxylic acid. 3 Mol/l of $H_2SO_4$ was added to the resultant mixture to adjust its pH value to 4.0 thereby forming the $C_{13}$ dicarboxylic acid completely, heated to 80° C., and cooled at a standstill to room temperature. After filtration, washing and drying, a purified $C_{13}$ dicarboxylic acid product was obtained. The properties of the product are shown in Table 1.

EXAMPLE 6

To 200 ml of a fermentation liquid having a concentration of 35 g/l of C18 dicarboxylic acid and a pH value of 8.2, which had been fermented with *candida tropicalis,* was added 3 mol/l of $H_2SO_4$ to adjust its pH value to 3.0, heated to 90° C. and placed at a standstill for 30 minutes. Then the alkane remaining in the solution was separated. The solution was cooled down to room temperature. After filtration and washing, a filter cake of $C_{18}$ dicarboxylic acid containing mycelia was obtained.

130 Ml of water was added to the filter cake and mixed thoroughly. To the resultant mixture was added 10 mol/l of NaOH to adjust its pH value to 7.0, and heated to 95° C., then the temperature was reduced to and maintained at 80° C. for 30 minutes, and thereafter cooled slowly to room temperature. After filtration a filter cake of monosodium salt of dicarboxylic acid and a filtrate was obtained. 1 Wt % of active carbon powder was added to the filtrate and the filtrate was treated for adsorption at 40° C. for 30 minutes. Then the filtrate was filtered again to obtain another filtrate that was then mixed with the above filter cake. To the resultant mixture was added 10 mol/l of NaOH to adjust its pH value to 10.7 and heated to 60° C. Then 2 wt % of siliceous earth was added and mixed thoroughly. Solids were filtered off. To the clarified filtrate was added 3 mol/l of $H_2SO_4$ to adjust its pH value to 3.0, heated to 80° C. and cooled to room temperature at a standstill. After filtration, washing and drying, a purified $C_{18}$ dicarboxylic acid product was obtained. The properties of the product are shown in Table 1.

TABLE 1

Properties of the product obtained according to the present invention

| Ex. No. | Content of total acid (wt %) | Content of diacid | Alkane content in product | Chroma | Nitrogen content (μg/g) | Yield of product (wt %) | Appearance of product |
|---|---|---|---|---|---|---|---|
| Example 1 | 99.17 | 97.93 ($C_{10}$) | undetectable | 24 | 24.7 | 90.8 | white |
| Example 2 | 99.1 | 98.2 ($C_{13}$) | undetectable | 32 | 23.2 | 90.3 | white |
| Example 3 | 99.35 | 98.7 ($C_{13}$) | undetectable | 28.5 | 34.2 | 93.2 | white |
| Example 4 | 99.4 | / | undetectable | 25.3 | 29.8 | 92.5 | white |
| Example 5 | 99.2 | 98.3 ($C_{13}$) | undetectable | 31 | 22.8 | 90.2 | white |
| Example 6 | 98.55 | 96.16 ($C_{18}$) | undetectable | 34 | 29.2 | 90.2 | white |

In table 1, total acid was determined by titrimetry, dicarboxylic acid was determined by gas chromatography using an internal standard, alkane was determined by gas chromatography, chroma was measured by platinum-cobalt colorimetry at dicarboxylic acid concentration of 20 g/l, and nitrogen is determined by chemiluminescence (total nitrogen).

What is claimed is:

1. A process for purifying long-chain dicarboxylic acids from a liquid containing a long-chain dicarboxylic acid and/or a salt thereof comprising the steps of:
   a. adjusting the pH value of said liquid containing a long-chain dicarboxylic acid and/or a salt thereof to 6.2–7.0 to form a monosalt of long-chain dicarboxylic acid;
   b. dissolving the monosalt of long-chain dicarboxylic acid by heating to obtain a solution containing the monosalt of long-chain dicarboxylic acid;
   c. crystallizing the solution obtained in step b by cooling, and filtering the solution to obtain a filter cake of the monosalt of long-chain dicarboxylic acid and a filtrate;
   d. dissolving the filter cake of the monosalt of long-chain dicarboxylic acid obtained in step c by heating;
   e. converting the monosalt of long-chain dicarboxylic acid into long-chain dicarboxylic acid; and
   f. isolating the long-chain dicarboxylic acid.

2. The process according to claim 1, wherein in step a said pH value is adjusted to 6.5–6.8.

3. The process according to claim 1, wherein said long-chain dicarboxylic acid is a $C_{10}$–$C_{18}$ long-chain dicarboxylic acid or a mixture of $C_{10}$–$C_{18}$ long-chain dicarboxylic acids.

4. The process according to claim 1, wherein the filtrate obtained in step III is treated with an adsorbent, and the treated filtrate is used for dissolving the filter cake in step d.

5. The process according to claim 1, wherein said liquid containing a long-chain dicarboxylic acid and/or a salt thereof is a fermentation liquid containing mycelia of an n-alkane.

6. The process according to claim 5, wherein prior to step a the mycelia are removed from the fermentation liquid and wherein in step a the pH value is adjusted with an acid to 6.2–7.0.

7. The process according to claim 1, wherein in step e the monosalt of long-chain dicarboxylic acid is converted into long-chain dicarboxylic acid by acidifying with an acid.

8. The process according to claim 5, wherein prior to step a the fermentation liquid is acidified directly and is filtered to obtain a filter cake of long-chain dicarboxylic acid containing mycelia, and an alkali solution is added to the filter cake.

9. The process according to claim 8, wherein in step e the monosalt of long-chain dicarboxylic acid is converted into long-chain dicarboxylic acid by the following steps:
  i). adding an alkali to form completely a solution of disalt of long-chain dicarboxylic acid;
  ii). filtering off the solids; and
  iii). acidifying the filtrate obtained in the above step to convert the disalt of long-chain dicarboxylic acid into long-chain dicarboxylic acid completely.

10. The process according to claim 8, wherein prior to step c the solution obtained in step b is filtered to obtain a filtrate containing monosalt of long-chain dicarboxylic acid and the filtrate is subjected to the crystallization of step c.

* * * * *